(12) United States Patent
Tualle (10) Patent No.: US 6,903,825 B2
(45) Date of Patent: Jun. 7, 2005

(54) METHOD FOR ANALYZING A DIFFUSING SAMPLE BY TIME RESOLUTION MEASUREMENT

(75) Inventor: Jean-Michel Tualle, Antony (FR)

(73) Assignee: Universite Paris 13, Villetaneuse (FR)

( * ) Notice: Subject to any disclaimer, the term of this patent is extended or adjusted under 35 U.S.C. 154(b) by 302 days.

(21) Appl. No.: 10/275,011

(22) PCT Filed: May 17, 2001

(86) PCT No.: PCT/FR01/01520

§ 371 (c)(1),
(2), (4) Date: Oct. 31, 2002

(87) PCT Pub. No.: WO01/88507

PCT Pub. Date: Nov. 22, 2001

(65) Prior Publication Data

US 2003/0107742 A1 Jun. 12, 2003

(30) Foreign Application Priority Data

May 18, 2000 (FR) .............................................. 00 06392

(51) Int. Cl.[7] .................................................. G01B 9/02
(52) U.S. Cl. ...................................................... 356/450
(58) Field of Search ................................. 356/450, 477, 356/484; 250/227.19, 227.27; 600/309, 316, 322, 323, 328, 364

(56) References Cited

U.S. PATENT DOCUMENTS 4,109,647 A * 8/1978 Stern et al. .................. 600/479
4,590,948 A * 5/1986 Nilsson ........................ 600/479
5,738,101 A * 4/1998 Sappey ........................ 600/476
6,181,429 B1 * 1/2001 Barberis et al. ............. 356/477

OTHER PUBLICATIONS

M. R. Hee et al., "Femtosecond Transillumination Optical Coherence Tomography", Optics Letters, US, Optical Society of America, Washington, vol. 18, No. 12, 15 juin 1993 (Jun. 15, 1993), pp. 950–952, XP000345900, ISSN: 0146–9592 p. 950.

L. Wang et al., "Time–Resolved Fourier Spectrum and Imaging in Highly Scattering Media", Applied Optics, US, Otical Society of America, Washington, vol. 32, No. 26, 10 Septembre 1993 (Sep. 10, 1993), pp. 5043–5048, XP000393405, ISSN: 0003–6935, p. 5043–p. 5044.

(Continued)

Primary Examiner—Gregory J. Toatley, Jr.
Assistant Examiner—Michael A. Lyons
(74) Attorney, Agent, or Firm—Young & Thompson (57) ABSTRACT

A method for analyzing a diffusing sample comprises steps of: a) illuminating the sample with temporally coherent and wavelength-modulated incident light beam; b) producing a succession of interference signals with the diffuse light; c) combining each interference signal with a reference signal $(\text{Ref}(t,\tau_0))$ generating a time port; d) extracting the continuous component of each signal characteristic of the predetermined delay $(\tau_0)$ derived form c); applying a nonlinear function on each of the continuous components of the signals characterizing the predetermined delay $(\tau_0)$; and f) averaging each of the images, with the non-linear function, of the continuous components of the signals characterizing the predetermined delay $(\tau_0)$. The invention is useful for observing organs of the human body.

13 Claims, 5 Drawing Sheets

OTHER PUBLICATIONS

T. Zhang et al., "Multipass Michelson Interferometer With the Use of a Wavelength–Modulated Laser Diode", Applied Optics, US, Optical Society of America, Washington, vol. 35, No. 28, 1 Octobre 1996 (Oct. 1, 1996), pp. 5650–5656, XP000629793, ISSN: 0003–6935, p. 5650; figure 2, p. 5652, colonne de droite, dernier alinea– p. 5653, colonne de gauche.

B. Chance et al., "Phase Measurement of Light Absorption and Scatter in Human Tissue", Review of Scientific Instruments, US, American Institute of Physics. New York, vol. 69, No. 10, Octobre 1998 (Oct. 1998), pp. 3457–3481, XP000830323, ISSN: 0034–6748, p. 3474, colonne de gauche, dernier alinea, p. 3476, colonne de gauche, dernier alinea; figures 12, 13.

* cited by examiner

METHOD FOR ANALYZING A DIFFUSING SAMPLE BY TIME RESOLUTION MEASUREMENT

FIELD OF THE INVENTION

The present invention relates to a method of analyzing a scattering sample by time resolved measurement of the light scattered within this sample.

BACKGROUND OF THE INVENTION

In the medical field, it is known to use light, especially with wavelengths located in the infrared region, in order to study in some depth the nature of biological tissue.

However, biological tissue is highly scattering at optical wavelengths, which tends to blur all information relating to its internal structure. Now, this structure influences the data and it may be necessary to assess this influence. For this, it is beneficial to study the dynamics of light propagation in biological tissue. To this end, it is known to send a very short light pulse to the medium to be studied and to carry out time resolved measurements of the scattered light. Time resolution provides valuable information concerning the structure of the medium.

The measurements may be carried out in reflectance or in transmittance.

The reflectance measurements are used especially in order to determine the oxygenation level of the blood hemoglobin.

The transmittance measurements are used especially for detecting cancerous tumors of the breast. The images obtained by time resolved transmittance measurement of the scattered light produce high contrast images making it possible for a tumor to be clearly detected therefrom. However, the spatial resolution of the images is relatively mediocre.

This limitation arises from the technology used for implementing the measurement. This is because the time resolution needs to be carried out over a very short time of about a few tens of picoseconds. Thus, such resolution requires highly sophisticated and expensive technologies.

In the known observation devices, the source producing the light pulse is adapted to provide a very brief pulse.

For example, in the device described in document U.S. Pat. No. 5,692,511, the light source used is a titanium-sapphire laser. The latter is very expensive. Furthermore, the detection is awkward to implement. The solution utilized in the device described in this document uses an avalanche photodiode connected to an electronic time gate in order to determine the number of photons transmitted during a particular time period. The avalanche photodiode has a relatively long time response which degrades the potential contrast of the time gate.

More generally, in devices for analyzing scattered light by time resolved measurement, it is common to use a source making it possible to produce brief pulses such as pulsed lasers, which are expensive.

Furthermore, means used for detecting the light present problems specific to each of them which do not allow satisfactory use of the device.

From these means of detecting the signal, it is possible to distinguish:

fast detectors with electronic processing of the signal coming from the detector, the relatively long response time of which considerably degrades the contrast of the time gate;

time amplitude converters in photon counting mode which require decreasing the signal in order to be placed in a suitable mode, which is not compatible with the short acquisition time;

optical gates with a nonlinear effect which require powerful lasers with low rates of about 10 Hz, which considerably limits the sensitivity;

slit scanning cameras which have very high time resolution (about 2 ps), but the dynamic range of which is not very high; and ultrafast intensified cameras, the time resolution of which is not very high (about 80 ps) for a low repetition rate (about 1 kHz).

Thus, currently available technologies do not make it possible to obtain good spatial resolution, especially with scattering tomography.

OBJECT OF THE INVENTION

The aim of the invention is to provide a device for analyzing a scattering sample by time resolved measurement of the scattered light, the implementational cost of which is modest.

SUMMARY OF THE INVENTION

To this end, the subject of the invention is a method of observing a scattering sample of the aforementioned type, characterized in that it comprises the steps of:

a) illuminating the sample with a temporally coherent and wavelength-modulated incident light beam;

b) producing a succession of interference signals, recorded over a time interval, by superposition of the scattered light obtained at the output of the sample and of light taken from the incident beam illuminating the sample;

c) combining each interference signal with a reference signal generating a time gate centered on a predetermined delay in order to produce a signal characteristic of the predetermined delay;

d) extracting the d.c. component ("continuous component") of each signal characteristic of the predetermined delay;

e) applying a nonlinear function to each of the d.c. components of the signals characteristic of the predetermined delay; and f) carrying out a linear combination of each of the images, with said nonlinear function, of the d.c. components of the signals characteristic of the predetermined delay.

According to particular embodiments, the method comprises one or more of the following characteristics:

said nonlinear function is a function chosen from the group consisting of square functions, and the absolute value function;

said nonlinear function is a function of at least two variables taken from the d.c. components of the signals characteristic of the predetermined delay obtained from the succession of interference signals recorded over the time interval;

for the combination of each interference signal with said reference signal, the incident beam is additionally amplitude modulated by means of an amplitude modulation introducing the predetermined delay;

for an amplitude modulation equal to the sum of said reference signal and of a reference signal with zero delay, said linear combination comprises a calculation subtracting from each of the images, with said nonlinear function, d.c. components of the signals characteristic of a zero delay;

said linear combination comprises calculating the mean of each of the images, with said nonlinear function, of the d.c. components of the signals characteristic of the predetermined delay;

when producing the succession of interference signals, a relative displacement is imposed between the incident beam and the scattering sample, the frequency of the imposed displacement being less than the frequency of the wavelength modulation of the light of the incident beam; and said reference signal comprises a sinusoidal function of the product of the predetermined delay on which the time gate is centered and of the wavelength modulation function of the incident beam.

The subject of the invention is also an apparatus for analyzing a scattering sample by time resolved measurement of the light scattered within this sample, characterized in that it comprises:

a) means for illuminating the sample with a temporally coherent and wavelength-modulated incident light beam;

b) an interferometer for producing a succession of interference signals, recorded over a time interval, by superposition of the scattered light obtained at the output of the sample and of light taken from the incident beam illuminating the sample;

c) means for combining each interference signal with a reference signal generating a time gate centered on a predetermined delay in order to produce a signal characteristic of the predetermined delay;

d) means for extracting the d.c. component of each signal characteristic of the predetermined delay;

e) means for applying a nonlinear function to each of the d.c. components of the signals characteristic of the predetermined delay; and f) means for carrying out a linear combination of each of the images, with said nonlinear function, of the d.c. components of the signals characteristic of the predetermined delay.

The invention also relates to equipment for measuring the content of a particular component in part of a living organism, comprising an apparatus for analyzing a scattering sample as described above, and means for calculating said content of a particular component as a function of the result of the analysis supplied by said apparatus.

According to a particular embodiment, said analysis apparatus is suitable for producing interference signals from the light backscattered by an organ of a human being or of an animal, and said calculating means are suitable for calculating the oxygenation level of this organ.

Finally, the subject of the invention is imaging equipment comprising:

as described above, an analysis apparatus which is suitable for producing and processing several successions of interference signals obtained from the light scattered in several adjacent regions of the sample and thus to supply an analysis result for each of the adjacent regions of the sample; and means for producing an image of the sample from the analysis result supplied for each of the adjacent regions of the sample.

According to a particular embodiment, said analysis apparatus is suitable for producing interference signals from the scattered light transmitted through an organ of a human being or of an animal.

BRIEF DESCRIPTION OF THE DRAWINGS

The invention will also be better understood on reading the following description, given solely by way of examples, and made with reference to the drawings in which.

DETAILED DESCRIPTION OF THE INVENTION

Figure 1:
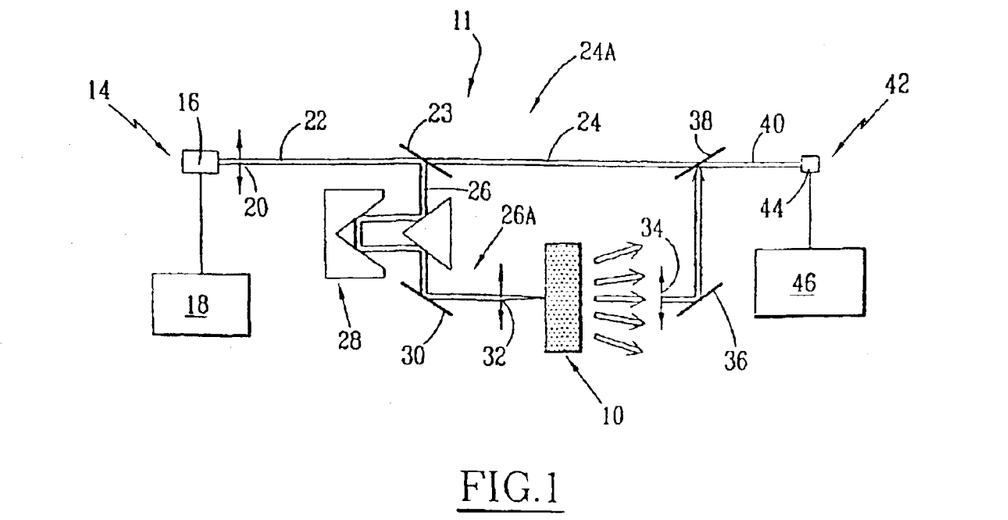
FIG. 1 is a schematic view of an analysis apparatus according to the invention.

The apparatus shown in FIG. 1 illustrates the principle of the analysis method according to the invention.

This apparatus makes it possible to analyze, in transmittance, a scattering sample 10 by time resolved measurement of the scattered light. It uses an interferometric technique to carry out the measurement and to this end, comprises an interferometer denoted by the general reference 11.

It is possible, by means of the apparatus, to reconstruct the time variation of the scattered energy with time resolutions of about 50 ps to 20 ps.

More specifically, the apparatus uses a temporally coherent and wavelength-modulated light source 14 so as to simulate, by suitable processing of the detected interference signal, an incoherent source.

The source 14 comprises a laser cavity 16 connected to a control unit 18 suitable for modulating the wavelength of the beam produced by the laser cavity 16. The laser cavity 16 is, for example, a laser diode or an extended cavity laser diode. It is suitable for producing a temporally coherent monochromatic light beam.

The central emitting wavelength is chosen depending on the applications. According to a particular embodiment of the method, several different central wavelengths are successively used, thus making it possible to carry out spectroscopic measurements. The wavelengths are, for example, equal to 780 nm and 850 nm for analysis of the oxygenation level of the tissue.

The control unit 18, whose practical embodiment is within the scope of a person skilled in the art, is suitable for periodic modulation of the wavelength of the beam produced by the diode 16. This modulation is advantageously a sinusoidal modulation. The amplitude $\delta\lambda$ of this modulation is of the order of a few hundredths of a nanometer.

The temporal resolution $\Delta t$ obtained for a modulating amplitude $\delta\lambda$ of a few hundredths of a nanometer is about $\Delta t = 2\lambda^2/(\pi c \delta\lambda)$, that is to say a few tens of picoseconds.

Advantageously, the light produced by the diode 16 is modulated continuously, thereby avoiding mode jumps.

The modulating frequency f is chosen to be fast enough so that the scattering medium can be considered as immobile during the modulating period $f^{-1}$. The modulating frequency is advantageously between 0.1 and 10 kHz and is, for example, chosen to be 1 kHz.

A lens 20 may be provided at the output of the diode 16 in order to adjust the width of the incident beam produced by the diode. The incident beam, denoted 22, is sent toward the interferometer 11 which comprises, at the input, a semireflecting mirror 23 which separates the incident beam 22 into two beams 24 and 26. These two beams 24, 26 propagate respectively along a reference arm 24A of the interferometer and along another arm 26A containing the sample.

In the arm 26A, the beam 26 is first sent into an optical system, known per se, which makes it possible to adjust the step difference between the optical paths of the two arms of the interferometer. At the output of the adjustment system 28, the beam 26 is sent via a mirror 30 onto the sample 10 forming the scattering medium. A lens 32 may advantageously focus the beam onto a given point of the sample.

Means 34 for collecting the scattered beam, such as a convergent lens, collect the beam at the output of the sample 10. The scattered light is then sent, via a mirror 36, to a semireflecting mirror 38 which superimposes the scattered beam and the beam 24 propagated along the reference arm of the interferometer.

Advantageously, the interferometer 11 comprises means making it possible for the position of the beam 26 arriving on the sample 10 to be continuously slightly modified. The position of the beam is modified during the analysis, to increase the accuracy thereof, as will be explained below.

These means comprise, for example, components for moving the mirror 30 and/or the convergent lens 32, so as to modify the position of the beam on the sample and/or the angle of incidence of the beam with respect to the sample.

Similarly, the interferometer advantageously comprises, downstream of the sample 10 in the arm 26A, means making it possible to modify the region collecting the scattered light, on the sample. These means comprise, for example, components for moving the collection means 34 or the mirror 36.

The beam denoted 40, obtained by superposition, at the output of the interferometer 11, is sent to detection and analysis means 42.

Figure 2:
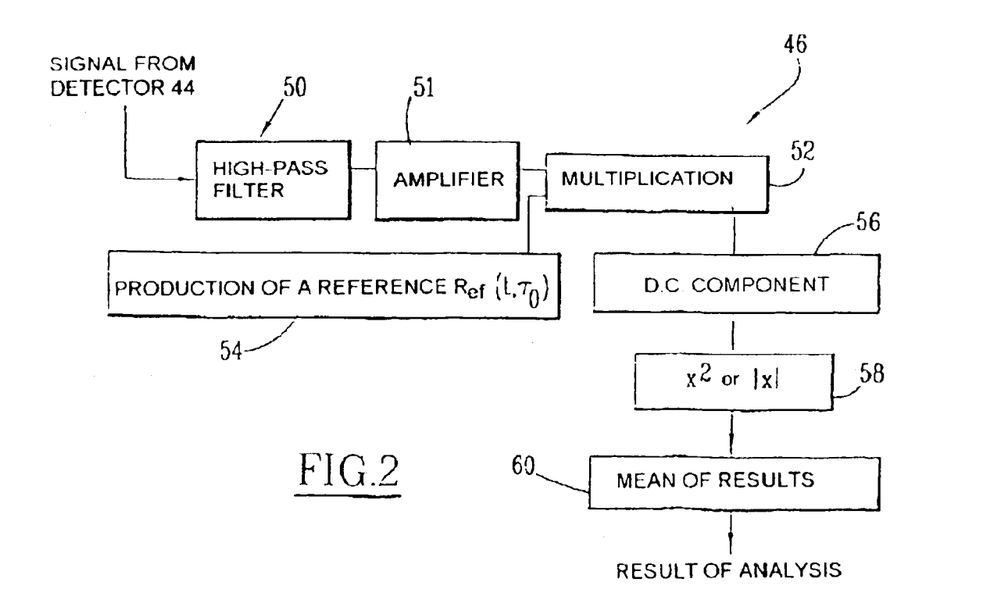
FIG. 2 is a flow chart illustrating the structure of the data processing unit of the detector of the apparatus of FIG. 1.

These means 42 comprise a detector 44 connected to a data processing unit 46, the main means of which are described with respect to FIG. 2.

The detector 44 is, for example, a photodiode.

Advantageously, the characteristics of the optical systems placed in the arm 26A of the interferometer, downstream of the sample 10, are chosen so that the coherent surface of the scattered beam at the detector 44 is of the same order of magnitude as the active surface of this detector.

In the embodiment described, the data processing unit 46 is formed from an assembly of analog electronic circuits suitable for providing the functions described with respect to FIG. 2.

At the input, the unit 46 comprises a high-pass filter 50 in order to filter the signal collected by the detector 44. The cut-off frequency of the filter 50 is of the order of one to ten times the modulation frequency f of the light emitted by the diode 16. In the present case, the cut-off frequency is of the order of one kilohertz.

The main objective of the high-pass filter 50 is to remove the d.c. component of the signal. It also eliminates low-frequency interference and possible interference effects related to the wavelength modulation of the diode 16. The interference signal obtained at the output of the filter 50 has a much higher frequency than the modulating frequency.

The signal obtained at the output of the filter is advantageously amplified by an optional amplifier 51.

Although the filter 50 is advantageously used, the latter may be omitted.

A multiplication stage 52 is provided at the output of the amplifier 51. It multiplies the filtered signal by a reference signal $Ref(t,\tau_0)$. The signal $Ref(t,\tau_0)$ comes from a device 54 for producing this signal. This device is, for example, a programmable signal generator or an analog electronic circuit consisting of a set of oscillators, the characteristic parameters of which can be adjusted.

The output of the multiplication stage 52 is connected to a stage 56 for extracting the d.c. component (or "continuous component") of the signal, that is to say, for calculating its mean value.

The signal $Ref(t,\tau_0)$ is such that the d.c. component of the product of the reference signal $Ref(t,\tau_0)$ and of the signal measured by the detector 44, in the absence of scattering medium in the second arm 26A of the interferometer, is essentially zero, except if the delay $\delta t$ between the two arms of the interferometer is approximately equal to $\tau_0$, to within $\Delta t$, where $\Delta t$ is the time resolution. The delay $\delta t$ corresponds to the difference in optical path length between the two arms of the interferometer 11 in the absence of a scattering sample, divided by the velocity of light.

The combination of the interference signal and of the reference signal $Ref(t,\tau_0)$ acts as a time gate centered on the delay $\tau_0$, this gate selecting the component of the interference signal corresponding to a delay $\tau_0$ with respect to the time for travelling through the reference arm 24A of the interferometer.

The signal $Ref(t,\tau_0)$ is, for example, expressed in the form:

$$Ref(t,\tau_0) = A\ \sin^n(2\pi f\ t)\cos(\delta\lambda_0\tau_0\ \cos(2\pi f\ t)+\phi)$$

for modulation of the light emitted by the diode 16 being expressed in the form $\delta\lambda(t)=\delta\lambda_0\ \cos(2\pi f\ t)$.

Several values of A, n and $\phi$ are possible. For example, the following values are suitable: A=1, n=4 and $\phi=0$.

According to a variant embodiment, the signal $Ref(t,\tau_0)$ is produced using an optical interferometer without a sample and having a delay $\tau_0$ between the two arms, by filtering the d.c. component of the signal detected at the output of the interferometer and by multiplying the result by another function generated by an analog electronic device, this function canceling itself out at the extrema of the modulation $\delta\lambda(t)$. This other function will, for example, be $\sin^n(2\pi ft)$ In a stage 56, the extraction of the d.c. component of the product calculated in stage 52 is obtained, for example, by using a low-pass filter. In this case, the signal extracted is a d.c. signal whose variation with time is a slow variation associated with movements of the sample 10 or with movements of the optical systems 30, 32 and/or 34, 36.

As a variant, the extraction of the d.c. component is provided by an integrating device which integrates the signal obtained at the output of stage 52 for exactly a whole number of half-periods $f^{-1}/2$. In this case, the signal from stage 56 is sampled after each integration of this type.

The data processing unit further comprises a stage 58 for applying a nonlinear function to the d.c. component of the signal obtained at the end of stage 58. This function is, for example, a square function, or a function raised to any other even power, or else the application of the absolute value function.

The application of such a function leads to considering just the amplitude of the signals, independently of their sign and to allowing their mean not to be zero.

Figure 3:
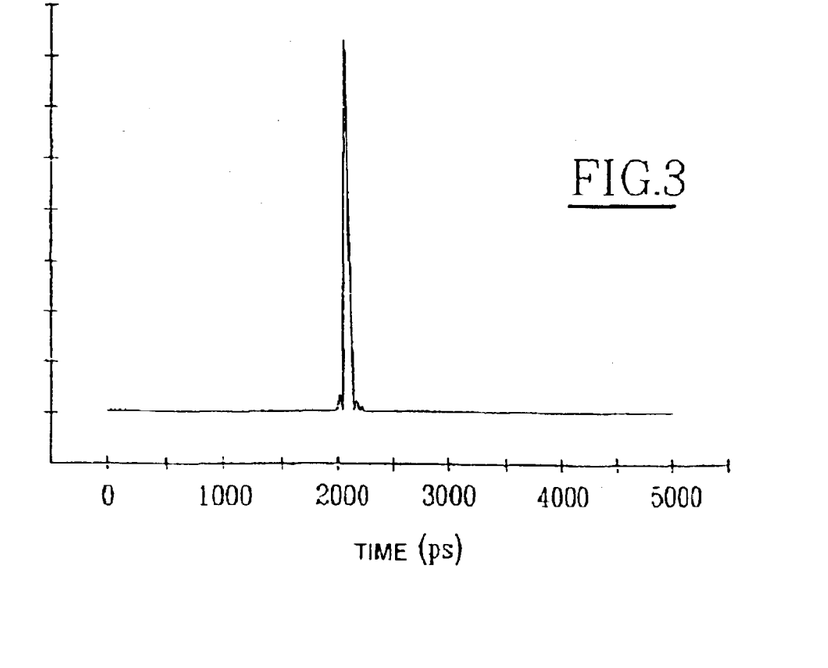
FIGS. 3, 4, 5 and 6 are curves illustrating the shape of signals which can be obtained at various points of the data processing unit of FIG. 2, in the presence and in the absence of a scattering medium.
Figure 4:
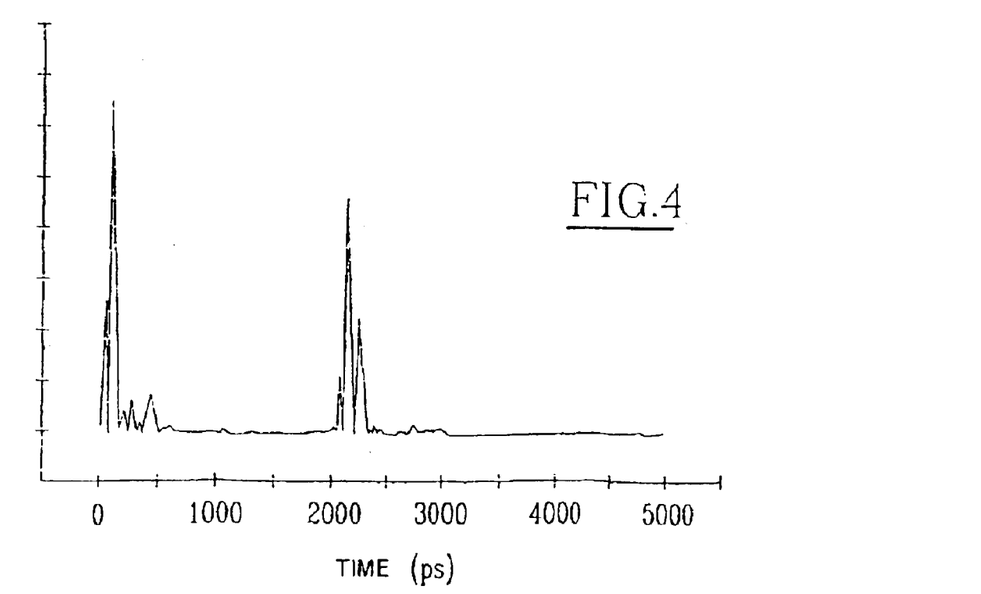

The result of applying the time gate used during the multiplication carried out by stages 52 to 58 is illustrated in FIGS. 3 and 4. The signal represented in these figures is the d.c. component obtained at the output of stage 58, as function of the value of the predetermined delay $\tau_0$.

The signal shown in FIG. 3 is obtained from the apparatus of FIG. 1, in which no sample is placed in the arm 26A.

In the example considered in this figure, the top of the peak corresponds to a delay substantially equal to 2080 ps, this value corresponding to the delay $\delta t$ between the two arms of the interferometer.

In contrast, the signal shown in FIG. 4 is obtained, at the output stage 56, in the presence of a scattering medium placed in the branch 26A of the interferometer.

On this curve, the presence of a nonzero signal is noticed in the vicinity of the value $\delta t$ of the delay between the two arms of the interferometer.

In this figure, a first signal close to the time origin is also noticed, this signal corresponding solely to the scattered light coming from the arm 26A, independently of interference with the reference coming from the arm 24A. This signal is not used for implementing the method.

The following stage denoted 60 of the unit 46 is suitable for establishing the mean of the signals obtained at the output of stage 58 for a particular duration. The mean calculated by stage 60 is determined for a duration of about a second. To this end, stage 60 comprises, for example, a low-pass filter.

As a variant, calculation of the mean is replaced by simply adding sampled signals, coming from stage 58 or any other form of linear combination carried out on these signals.

The signal obtained at the end of stage 60 for a given value of the predetermined delay $\tau_0$ is proportional to that part of the scattered energy which has a delay $\tau_0$ with respect to the time of travel through the reference arm 24A of the interferometer, to within $\Delta t$.

Figure 5:
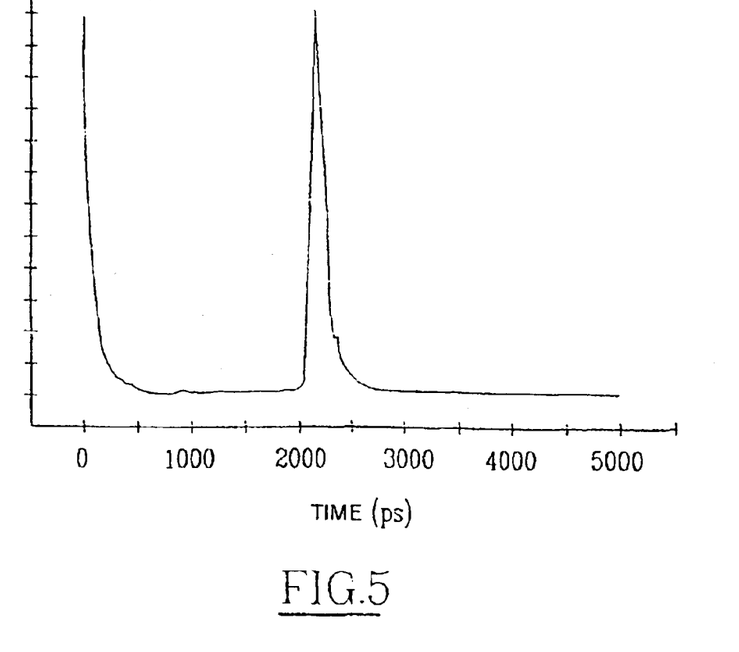

FIG. 5 shows an example of the signal obtained at the output of stage 60, as a function of the predetermined delay $\tau_0$. This figure clearly shows a signal for values of the predetermined delay $\tau_0$ greater than the delay $\delta t$ between the two arms of the interferometer.

Because of the mean calculated at the end of applying a nonlinear function to the signals obtained at the output of the time gate, the profile of the curve of FIG. 5 shows a clear profile representing the structure of the scattering medium.

The delay $\tau_0$ makes it possible to determine the time needed for the beam to pass through the sample, for example, by simply subtracting, from the delay $\tau_0$, the delay time $\delta t$ between the two arms of the interferometer, and by adding a correction associated with the sample thickness.

Figure 6:
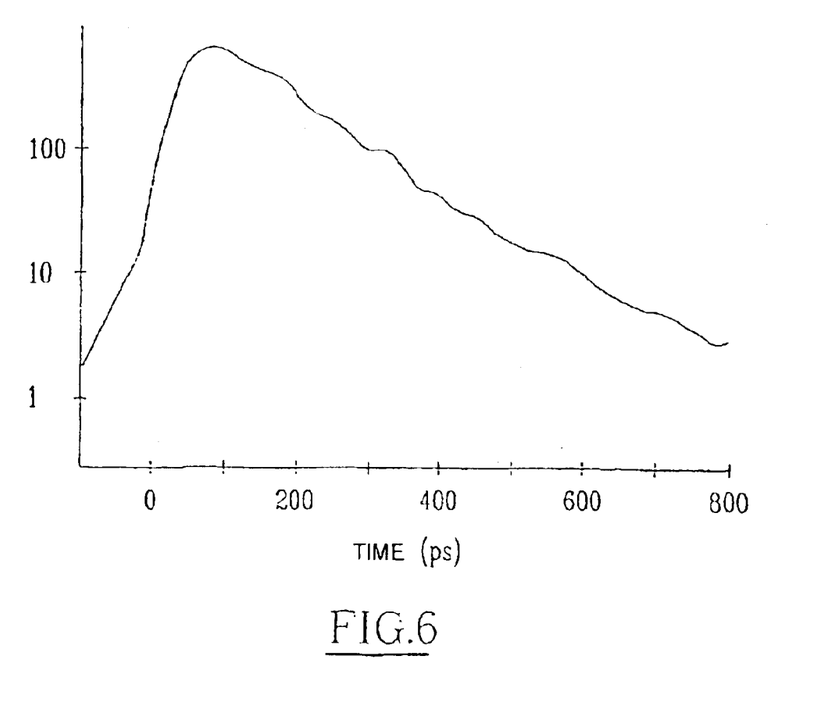

The signal of FIG. 5 is shown on a larger scale in FIG. 6, where the time origin has been corrected for the delay $\delta t$ between the two arms of the interferometer.

The time variation of the calculated mean value is associated with a transformation of the relevant parameters in the medium studied.

According to a particular embodiment, the apparatus comprises several data processing units 46, each one associated with a delay value $\tau_0$, this making it possible to obtain measurements of the scattered energy for different delays $\tau_0$.

The data processing unit 46, described above, consists of an analog electronic device. However, as a variant, this data processing unit comprises an analog high-pass filter 50, at the output of which an analog/digital converter is provided. All the processing carried out by stages 52 to 60 is then carried out in a completely digital manner by implementing a suitable algorithm in a computer. In this case, the different number of values $\tau_0$ for which the calculation is carried out may be very large.

During the measurement, the signal obtained at the output of stage 58 fluctuates over the same time scale as the signal obtained at the output of stage 56. These fluctuations are due to the movements in the scattering medium itself when this medium is a biological medium. These movements induce fluctuations over time scales of about a millisecond.

Now, these fluctuations are desirable in order that the mean value obtained at the output of stage 60 is as accurate as possible. This is because these fluctuations make it possible to measure various values in order to take the mean thereof. This mean will be closer to its theoretical value, which is the time resolved scattered intensity, the larger the number of different values obtained by the fluctuations.

Thus, advantageously, if the fluctuations of the medium are insufficient or too slow, additional fluctuations are induced by moving the beam 26 by displacing the mirror 30, the lens 32, the collection means 34 and/or the mirror 36.

The movement is controlled such that the time scale of the time fluctuations is greater than the modulation period $f^{-1}$. Thus, the frequency of beam displacement is less than that of the wavelength modulation of the incident light.

An observation apparatus using an interferometer, and means of emitting a temporally coherent and wavelength-modulated light beam, together with processing means as described above, may advantageously be used for measuring, by reflectance, the oxygenation level of the hemoglobin of a human being.

To measure this oxygenation level, two wavelengths $\lambda_1$ and $\lambda_2$ are necessary.

Figure 7:
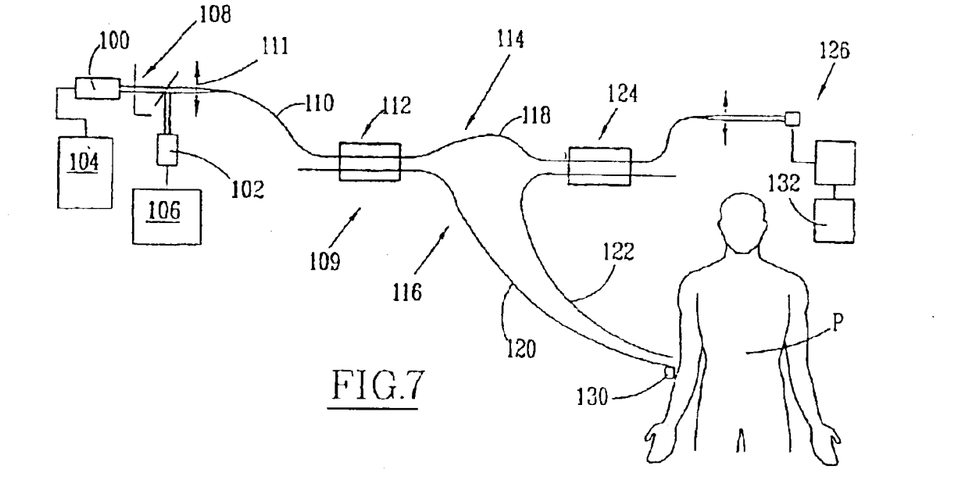
FIG. 7 is a schematic view of equipment for measuring by reflectance the oxygenation level of hemoglobin implementing a method according to the invention.

To this end, the equipment for measuring the oxygenation level illustrated in FIG. 7 comprises a first laser diode 100 and a second laser diode 102, the central emitting wavelengths of which are respectively $\lambda_1$ and $\lambda_2$. These two diodes are each controlled by a control unit 104 and 106 making it possible to modulate the wavelength of the emitted light, as described in the previous embodiment.

An automatic shutter 108 is placed at the output of the laser diodes 100 and 102 in order to selectively illuminate an interferometer denoted 109 with one or other of the light beams emitted by these diodes.

The output of the automatic shutter 108 is coupled to an optical fiber 110 by suitable coupling means 111. The fiber 110 is a monomode optical fiber.

The fiber 110 routes the light to a 50/50 coupler denoted 112 making it possible to separate the incident light and to direct the latter along the two arms denoted 114 and 116 of the interferometer.

The reference arm 114 is formed by a monomode optical fiber 118.

The second arm 116 comprises a monomode optical fiber 120 forming an emitting fiber making it possible to direct the incident beam to the sample to be studied. In the present case, the end of the optical fiber is placed on the arm of a patient.

Downstream of the sample to be studied, the second arm 116 of the interferometer comprises a second monomode optical fiber, denoted 122, constituting an optical fiber for collecting the scattered light. Its free end is placed close to the free end of the emitting fiber 120 so as to collect the backscattered scattered light. The optical fibers 118 and 122 are connected to each other by a 50/50 coupler, denoted 124, making it possible to superimpose the light beams transmitted in the two arms of the interferometer.

The output of the coupler 124 is connected to detection and analysis means 126 similar to the means 42 of the embodiment of FIG. 1.

Advantageously, an optional vibrator 130 is applied to the emitting optical fiber 120 and/or the receiving fiber 122 so as to cause a slight displacement of the latter during analysis in order to cause fluctuations of the signal and thus to improve, as explained above, the accuracy of the measurement carried out.

Preferably, for each wavelength $\lambda_1$, $\lambda_2$, the scattered light is measured for various delays $\tau_0$, as described with respect to the embodiment of FIG. 1.

The equipment comprises, connected to the detection and analysis means 126, a unit 132 for calculating the oxygenation level of the hemoglobin.

The oxygenation level of the hemoglobin is deduced from the absorption coefficients of the medium calculated at the two wavelengths $\lambda_1$, $\lambda_2$ specific to the diodes 100 and 102. The absorption coefficient is calculated, as a function an equation known per se, from the exponential decay of light scattering as a function of time, this decay being defined from various measurements carried out at different delays $\tau_0$.

Figure 8:
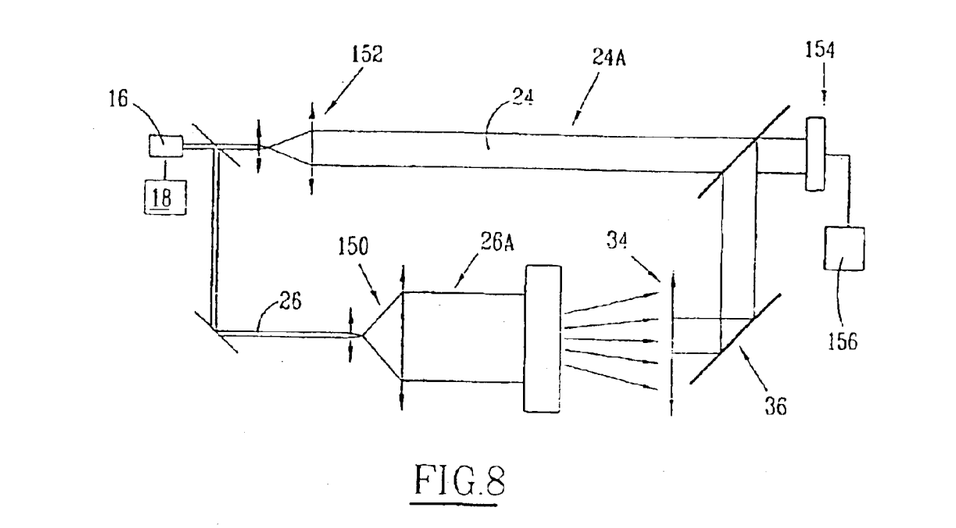
FIG. 8 is a schematic view of imaging equipment in transmittance implementing a method according to the invention.

While the apparatuses illustrated in FIGS. 1 and 7 only allow a time resolved measurement to be carried out at any point in question of the sample, the apparatus illustrated in FIG. 8 is imaging equipment making it possible to produce a two-dimensional image of the sample studied.

This equipment adopts a structure substantially similar to that of the apparatus of FIG. 1. Thus, elements identical or similar to those of this embodiment are denoted by the same reference numbers.

In this imaging equipment, the arm 26A of the interferometer, in which the sample is placed, comprises, upstream of the sample, a telescope 150 enabling the beam 26 propagating along the arm to be enlarged. Thus, most of the sample surface is illuminated by the incident beam.

Similarly, the reference arm 24A of the interferometer has a telescope 152 also enlarging the diameter of the beam 24 propagating along this arm.

The localized sensor 44 used in the embodiment is in this case replaced by an array of independent sensors or pixels 154. This array comprises a set of sensors distributed in lines and in columns. Each detection sensor is associated with an integrated circuit which forms the high-pass filter 50 and amplifies the signal. The signal from each sensor filtered and amplified in this way is then multiplied by the reference signal Ref(t,$\tau_0$) then integrated over a whole number of half periods in order to extract the d.c. component therefrom. After this, the steps of calculating a nonlinear function and the mean of the results of this function are advantageously carried out digitally for each sensor.

The set of results obtained for each sensor is sent to a suitable unit 156 in order to produce an image of the sample studied as a function of the results received.

The value of the delay $\tau_0$ is advantageously adjusted so as to obtain a high-contrast image by selecting the scattered light at short times.

Advantageously, the telescope 150 and the collector system 34, 36 are combined with means making it possible to alter their inclination with respect to a reference axis so as to obtain images in transmittance in different directions and thus to allow a three-dimensional reconstruction of the medium from images obtained of the sample for various positions of the telescope 152 and of the collector system 34, 36.

The equipment of FIG. 8 is designed, in particular, for observing an organ of a human being or animal by transmittance. It is especially used for searching for cancerous tumors of the breast.

The apparatuses described here and the method which they implement make it possible to analyze a scattering sample by time resolved measurement of the light scattered in this sample for a very low cost.

This is because the light source used can be formed from a single laser diode. Similarly, the detection and analysis means may be produced at low cost.

Furthermore, with the wavelength-modulated light used, the electromagnetic fields are much less intense than in a pulsed regime, as is the case in the prior art.

Finally, great sensitivity may be obtained by virtue of the interferometric nature of the analysis.

Even with a single photodiode as detector, very high sensitivity and a very dynamic range may be obtained.

Figure 9:
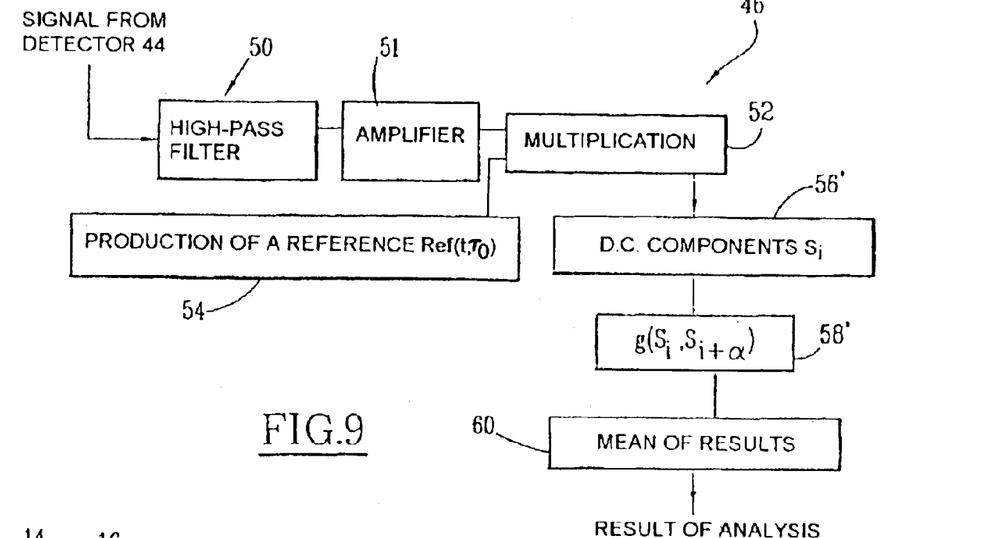
FIG. 9 is a view similar to that of FIG. 2 illustrating a variant of the data processing unit of the detector of the apparatus of FIG. 1.

FIG. 9 illustrates a variant of the analysis method according to the invention designed to obtain a time resolved measurement of a quantity relating to the light scattered in the sample to be analyzed. This variant is distinguished from the method described with respect to FIGS. 1 to 6 solely by the structure of the data processing unit 46 at its stages 56 and 58.

The output from the multiplication stage 52 is connected to a stage 56' for extracting respective d.c. components of the signals obtained at the output of stage 52 for a particular duration, substantially equal to that retained for determining the mean calculated by stage 60 in the method described with respect to FIG. 2. The d.c. components thus obtained in stage 56' are denoted $S_i$, where i denotes the $i^{th}$ signal output from stage 52 during the aforementioned duration. The means implemented to obtain each d.c. component $S_i$ are similar to those explained above.

The output from this stage 56' is connected to a stage 58' for applying a nonlinear function g to at least two variables taken from the d.c. components $S_i$ from stage 56'. It should be noted that the term "nonlinear" is in this case considered in a broad sense, that is to say, in the case of functions with several variables, only functions which are linear with respect to their variables taken overall in vectorial form, such as the function "sum of two vectors" for example, are excluded.

This nonlinear function is, for example, a product function applied to two distinct values $S_i$. Thus, it is possible to consider the function $g(S_i, S_{i+\alpha})=S_i \times S_{i+\alpha}$ where $\alpha$ is a positive nonzero integer. Such a function is suitable for studying the time variation of the value $S_{i+\alpha}$ with respect to the value $S_i$. This because, as has been explained above, a biological medium is the source of many movements and, in spite of practical precautions especially consisting in choosing a modulation frequency of the laser source 14 which is high enough to consider the scattering medium 10 as immobile during the modulating period, the signal $S_{i+1}$ recorded following a signal $S_i$ is slightly different from this signal $S_i$. The signal $S_{i+2}$ is even more so. More generally, a decorrelation of the signals $S_{i+\alpha}$ and $S_i$ is noted for $\alpha \geq 1$. The time variation of this decorrelation as a function of $\alpha$ and of $\tau_0$ directly provides useful data relating to the nature and intensity of movements in the analyzed medium 10.

To this end, the output from stage, 58' is connected to stage 60 for finding the mean of signals obtained at the output of stage 58', which mean is a function, on the one hand, of the delay $\tau_0$, as previously, and on the other hand, of the value of the integer α. A means for studying the decorrelation of signals $S_i$ from each other consists in following the time variation of this mean from stage 60, for increasing α and fixed $\tau_0$, for example.

In the case of measuring the oxygenation level of the hemoglobin of a human being, illustrated in FIG. 7, the data relating to the decorrelation of signals $S_i$ provide information on the blood circulation in tissues such as the muscle capillaries, in addition to measuring the oxygenation level as explained with respect to FIG. 7. The time resolved acquisition of these data makes it possible, for example, to isolate the contribution from the blood circulation in such capillaries with respect to that in larger blood vessels.

In the case of searching for cancerous tumors illustrated in FIG. 8, data relating to the decorrelation of signals $S_i$ provides information on the vascularization state of a tumor observed by the equipment of FIG. 8. Generally, such tumors are over-vascularized. The contrast of the image of the sample studied may thus be improved by using these decorrelation data.

Figure 10:
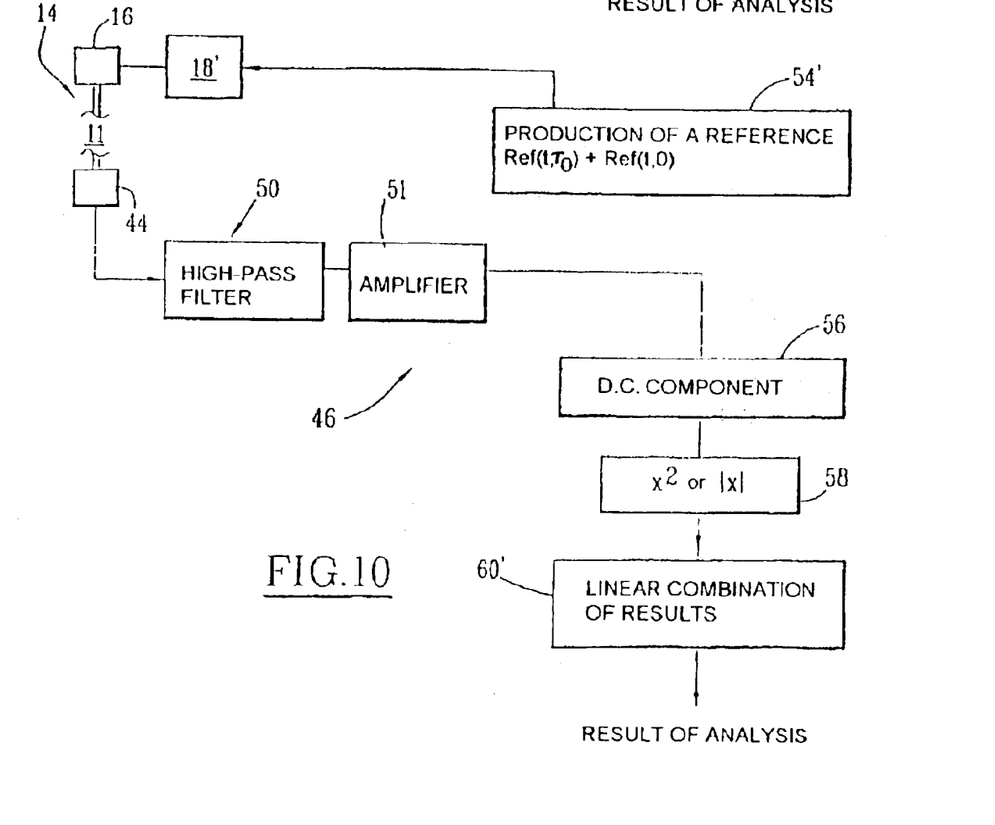
FIG. 10 is a schematic view of an alternative apparatus according to the invention associated with a flow chart of a type similar to that of FIG. 2 illustrating the structure of the unit for processing data detected by this alternative apparatus.

FIG. 10 illustrates a second variant of the analysis method according to the invention in which the means of combining the interference signal with the reference Ref(t,$\tau_0$) consist of means for modulating the amplitude of the laser source 16. More specifically, this variant of FIG. 10 is only differentiated from the embodiment described with respect to FIGS. 1 and 2 by the following.

First of all, the control unit 18 is replaced by a control unit 18' adapted so that it can both wavelength-modulate the beam produced by the laser cavity, in a manner substantially similar to the unit 18 of FIG. 1, and amplitude-modulate this laser beam, in an independent manner, from an external amplitude modulation signal. Producing such a control unit 18' is within the scope of a person skilled in the art, for example, in the case of using an extended cavity laser diode 16.

According to the invention, this additional amplitude modulation is capable of introducing, into the analysis apparatus, the reference signal Ref(t,$\tau_0$). To this end, a device 54' for producing a signal Ref(t,$\tau_0$)+Ref(T,0) is provided, of a type substantially similar to the device 54 of FIG. 2. This device 54' is connected to the control unit 18' in order to supply the external amplitude modulation signal.

At the output of the filtering 50 and amplification 51 stages, the recorded interference signal is then presented directly in the form of a combination, especially a product, comprising on the one hand a first term of a type similar to that from stages 50 and 51 of FIG. 1, that is to say a first term carrying the wavelength-modulated information and, on the other hand, a second term of a type similar to that from the device 54 of FIG. 1, that is to say a second term carrying the delay $\tau_0$. The combined signal thus obtained is characteristic of the delay $\tau_0$.

Moreover, the stage 60 of finding the mean of signals from stage 58 of FIG. 1 is replaced by a stage 60' adapted both to produce such a mean, and to subtract from the result obtained, the mean value corresponding to the processing by stages 56 and 58 of a signal characteristic of a delay $\tau_0=0$, that is to say a zero delay. This stage 60' therefore only produces a linear combination of the results from stage 58.

In this way, the results at the output of stage 60' are identical to those from stage 60 of FIG. 2.

This variant makes it possible to simplify the unit 56 for processing interference signals. For example, for the imaging equipment of FIG. 8, this variant makes it possible to simplify the array of sensors 154, each sensor being associated with an integrated circuit which filters, amplifies and extracts the d.c. component, with acquisition over a half period, of each interference signal. It is then possible to use a CCD camera as means 156 for producing an image of the sample studied.

Another variant (not shown) of the analysis method according to the invention consists in combining the two variants of FIGS. 9 and 10 together and, especially in the variant of FIG. 10, in replacing steps 56, 58 by steps 56', 58'.

Moreover, various layouts of the interferometric assembly 11 can be envisioned, in so far as they arise from the knowledge of a person skilled in the art. For example, the superposition mirror 38 may produce two beams 40, each of these two beams being detected by a respective sensor 44. The difference obtained between these two detected beams gives information similar to that previously coming from the single sensor, but advantageously with less noise.

What is claimed is:

1. A method of analyzing a scattering sample by time resolved measurement of the light scattered within this sample, characterized in that it comprises the steps of:

a) illuminating the sample with a temporally coherent and wavelength-modulated incident light beam;

b) producing a succession of interference signals, recorded over a time interval, by superposition of the scattered light obtained at the output of the sample and of light taken from the incident beam illuminating the sample;

c) combining each interference signal with a reference signal (Ref(t,$\tau_0$)) generating a time gate centered on a predetermined delay ($\tau_0$) in order to produce a signal characteristic of the predetermined delay ($\tau_0$);

d) extracting the d.c. component of each signal characteristic of the predetermined delay ($\tau_0$);

e) applying a nonlinear function to each of the d.c. components of the signals characteristic of the predetermined delay ($\tau_0$); and f) carrying out, a linear combination of each of the nonlinear function images of the d.c. components of the signals characteristic of the predetermined delay ($\tau_0$).

2. The method as claimed in claim 1, characterized in that said nonlinear function is a function chosen from the group consisting of square functions and the absolute value function.

3. The method as claimed in claim 1, characterized in that said nonlinear function is a function of at least two variables taken from the d.c. components of the signals characteristic of the predetermined delay ($\tau_0$) obtained from the succession of interference signals recorded over the time interval.

4. The method as claimed in claim 1, characterized in that, for the combination of each interference signal with said reference signal ($R_{ef}$(t,$\tau_0$)), the incident beam is additionally amplitude modulated by means of an amplitude modulation introducing the predetermined delay ($\tau_0$).

5. The method as claimed in claim 4, characterized in that, for an amplitude modulation equal to the sum of said reference signal ($R_{ef}$(t,$\tau_0$)) and of a reference signal with zero delay ($R_{ef}$(t,0)), said linear combination, comprises a calculation subtracting from each of the nonlinear function images of d.c. components of the signals characteristic of a zero delay ($\tau_0=0$).

6. The method as claimed in claim 1, characterized in that said linear combination comprises calculating the mean of each of the nonlinear function images of the d.c. components of the signals characteristic of the predetermined delay ($\tau_0$).

7. The method as claimed in claim 1, characterized in that, when producing the succession of interference signals, a relative displacement is imposed between the incident beam and the scattering sample, the frequency of the imposed displacement being less than the frequency of the wavelength modulation of the light of the incident beam.

8. The method as claimed in claim 1, characterized in that said reference signal ($R_{ef}(t,\tau_0)$) comprises a sinusoidal function of the product of the predetermined delay ($\tau_0$) on which the time gate is centered and of the wavelength modulation function of the incident beam.

9. An apparatus for analyzing a scattering sample by time resolved measurement of the light scattered within this sample, characterized in that it comprises:

a) means (16, 18; 100, 104, 102, 106) for illuminating the sample with a temporally coherent and wavelength-modulated incident light beam;

b) an interferometer (11; 109) for producing a succession of interference signals, recorded over a time interval, by superposition of the scattered light obtained at the output of the sample and of light taken from the incident beam illuminating the sample;

c) means (52, 54) for combining each interference signal with a reference signal ($R_{ef}(t,\tau_0)$) generating a time gate centered on a predetermined delay ($\tau_0$) in order to produce a signal characteristic of the predetermined delay ($\tau_0$);

d) means (56) for extracting the d.c. component of each signal characteristic of the predetermined delay ($\tau_0$);

e) means (58) for applying a nonlinear function to each of the d.c. components of the signals characteristic of the predetermined delay ($\tau_0$); and f) means (60) for carrying out a linear combination of each of the nonlinear function images of the d.c. components of the signals characteristic of the predetermined delay ($\tau_0$).

10. Equipment for measuring the content of a particular component in part of a living organism, comprising an apparatus for analyzing a scattering sample. according to claim 9, and means (132) for calculating said content of a particular component as a function of the result of the analysis supplied by said apparatus.

11. The equipment as claimed in claim 10, characterized in that said analysis apparatus is suitable for producing interference signals from the light backscattered by an organ of a human being or of an animal, and in that said calculating means are suitable for calculating the oxygenation level of this organ.

12. Imaging equipment comprising:

an analysis apparatus according to claim 9, which is suitable for producing and processing several successions of interference signals obtained from the light scattered in several adjacent regions of the sample and thus to supply an analysis result for each of the adjacent regions of the sample; and means (156) for producing an image of the sample from the analysis result supplied for each of the adjacent regions of the sample.

13. The equipment as claimed in claim 12, characterized in that said analysis apparatus is suitable for producing interference signals from the scattered light transmitted through an organ of a human being or of an animal.

* * * * *